United States Patent [19]
Yokoi et al.

[11] Patent Number: 5,881,714
[45] Date of Patent: Mar. 16, 1999

[54] HANDY TYPE ATOMIZER

[75] Inventors: Hiroyuki Yokoi; Masae Shibasaki, both of Saitama, Japan

[73] Assignee: A & D Company, Limited, Tokyo, Japan

[21] Appl. No.: 793,094

[22] PCT Filed: Oct. 7, 1995

[86] PCT No.: PCT/JP95/01368
§ 371 Date: Jul. 29, 1997
§ 102(e) Date: Jul. 29, 1997

[87] PCT Pub. No.: WO97/02856
PCT Pub. Date: Jan. 30, 1997

[51] Int. Cl.⁶ .................................................. A61M 11/00
[52] U.S. Cl. .................... 128/200.14; 128/200.18
[58] Field of Search ........................ 128/200.14, 200.16, 128/200.18

[56]  References Cited

U.S. PATENT DOCUMENTS

| | | | |
|---|---|---|---|
| 3,301,255 | 1/1967 | Thompson | 128/200.18 |
| 4,119,096 | 10/1978 | Drews | 128/200.16 |
| 5,134,993 | 8/1992 | van der Linden et al. | 128/200.16 |
| 5,152,456 | 10/1992 | Ross et al. | 128/200.16 |
| 5,261,601 | 11/1993 | Ross et al. | 128/200.16 |
| 5,452,711 | 9/1995 | Gault | 128/200.16 |
| 5,551,416 | 9/1996 | Stimpson et al. | 128/200.16 |

FOREIGN PATENT DOCUMENTS

| | | |
|---|---|---|
| 62-11627 | 3/1987 | Japan . |
| 3000139 | 5/1994 | Japan . |

*Primary Examiner*—Aaron J. Lewis
*Attorney, Agent, or Firm*—Sixbey Friedman Leedom & Ferguson; Thomas W. Cole

[57] ABSTRACT

A switch 70 is provided between the gripping casing of an atomizer and the cover thereof. Said switch 70 has a switch accommodating section 72 secured at the cover member 16, a switch operating section 74 protruding on the inner circumferential face of said cover, and a switch body 76 accommodated in said switch accommodating section 72. Said switch accommodating section 72 is formed to be square-tubular with both the ends thereof open, said switch operating section 74 is provided at the switch accommodating section 72 corresponding to the position thereof, and a waterproof cover 78 which is able to cover the outer circumference of the switch accommodating section 72 is provided at the lower end of the switch operating section 74. Said switch body 76 has a constantly open type switch mechanism 76a having a pair of contacts spaced from each other in a constant state, a rod 76b interlocked with the switch mechanism 76a and a spring 76c which presses the rod 76b upward. Said switch 70 operates when the cover is attached to the gripping casing, whereby power supply to the atomizing means and the feeding means will be enabled.

4 Claims, 6 Drawing Sheets

HANDY TYPE ATOMIZER

FIELD OF THE INVENTION

The present invention relates to a handy type atomizer and in particular relates to a technology for improving the safety thereof.

BACKGROUND OF THE INVENTION

An atomizer has been already known as an instrument used for treating the nose and throat, and this kind of an atomizer is, for example, utilized for treating primary catarrh, allergic rhinitis, etc. An atomizer used for such a therapy is such that heat or vibration is given to liquefied medicine in order to atomize the same and a patient is caused to inhale the same. A handy type and an installation type are available on the market.

Furthermore, various kinds of handy type atomizers are proposed in view of their portability, for example, several structural examples are disclosed in Japanese laid-open utility model publications Nos. 51541 of 1983, 109545 of 1986, 75750 of 1990, etc. An atomizer disclosed in Japanese laid-open utility model publication No. 51541 of 1983 is provided with a cylindrical casing in which an atomizer is incorporated, and the casing is such that the cross-section thereof connects a small-diametered semicircle with a large-diametered semicircle and is made cylindrical, and a nozzle which is able to discharge atomized medicine is provided in a fixed state at the small-diametered semicircle at the upper side of the casing.

With an atomizer having such a structure, when using the same, the large-diametered semicircle section of the casing is gripped by a hand and the nozzle secured at the small-diametered semicircle is caused to face the nose or throat. Furthermore, an atomizer disclosed by Japanese laid-open utility model publication No. 109545 of 1986 is provided with a casing formed to be roughly box-like, in which an atomizer is incorporated, and the width of the casing is made tapered from the rear end thereof toward the front end side, and a nozzle which is able to discharge atomized medicine is provided in a fixed state at the front end side.

With the atomizer having such a structure, when using the same, the rear end side is gripped by a hand and the nozzle at the front end side, which is made tapered, is caused to face the nose or throat. Furthermore, an atomizer disclosed by Japanese laid-open utility model publication No. 75750 of 1990 is provided with a cylindrical casing in which an atomizing means is incorporated, and a nozzle which is able to discharge atomized medicine is fixed at the upper side of the casing.

With an atomizer having such a structure, when using the same, the cylindrical casing is gripped by a hand and is caused to face the nose or throat. However, in such conventional atomizers, there still remain technical themes to be described below. That is, in the abovementioned utility model publications, since the nozzle is fixed in both of them, the atomizers are used while gripping the large-diametered semicircle section, the rear end section of the casing, or the cylindrical casing.

However, this kind of atomizer is used by not only an adult but also a child. With such a structure of an atomizer disclosed in the abovementioned publications, if the large-diametered semicircle side section, the rear end portion of the casing or a gripping section consisting of a cylindrical casing is set to a size suitable for an adult, the same is too large for use by a child, and it is difficult for a child to grip.

To the contrary, if the gripping section is set to a size suitable for a child, the size is not suitable for an adult, and it is difficult for an adult to use. Therefore, there is some parts thereof to be further improved for the convenience of use.

Therefore, the inventors developed a handy type atomizer which is able to solve these problems and already proposed the same with Japanese utility model application No. 54055 of 1991. With the atomizer according to this application, a gripping casing in which an atomizer is incorporated has a roughly gourd-shaped cross-section in which the small-diametered cylindrical portion is connected to the large-diametered cylindrical portion at the side, and a nozzle which is able to discharge atomized medicine is provided at the upper end side of the casing so that the discharge direction of the atomized medicine can be changed, whereby an adult patient is able to grip the large-diametered cylindrical portion thereof and a child patient is able to grip the small-diametered cylindrical portion thereof. Therefore, the convenience of using an atomizer is able to be much improved. However, it is found through a further consideration that another technical theme, which is described below, internally exists in the atomizer according to this application.

That is, with an atomizer according to the abovementioned application, since it is necessary to set liquefied medicine in a medicine disk secured in a gripping casing, there was a shortcoming that although the cover is detachably mounted in the casing, for example, in a case where the power source is erroneously switched on with the cover not completely attached in the casing when using the atomizer or the cover is erroneously removed from the casing during use, atomized medicine is splashed outside other than through the nozzle.

The present invention was developed in view of such shortcomings, and it is therefore an object of the invention to provide a handy type atomizer which is able to prevent atomized medicine from being splashed outside and is able to much increase the safety.

DISCLOSURE OF THE INVENTION

In order to achieve the above object, the invention provides a handy type atomizer having a medicine atomizing means, a nozzle for discharging atomized medicine outside, and a feeding means for sending medicine atomized by said atomizing means toward said nozzle side, which comprises a cylindrical gripping casing in which said atomizing means is incorporated, and a cover which is detachably mounted on the upper end of said gripping casing and has an attaching port of said nozzle, wherein a switch which is able to operate only when said cover is attached to said gripping casing and supply power to said atomizing means and feeding means is provided.

According to a handy type atomizer constructed as described above, since a switch is provided, which is able to operate only when said cover is attached to said gripping casing and supply power to said atomizing means and feeding means, the switch is not turned on in a case where the cover is removed from the casing or is not completely positioned in a correct position, and no power is supplied to said atomizing means and feeding means.

PREFERRED EMBODIMENTS OF THE INVENTION

Preferred embodiments of the invention are described in detail with reference to the drawings attached herewith. FIG. 1 through FIG. 5 show a preferred embodiment of a handy type atomizer according to the invention. An atomizer shown in these drawings has a medicine atomizing means 10, a nozzle 12 capable of discharging liquefied medicine atomized by said atomizing means 10, and a gripping casing 14. Said casing 14 has a small-diametered cylindrical portion 14a, a large-diametered cylindrical portion 14b and a bottom portion 14c and is formed so as to have a bottom. The casing 14 has a roughly gourd-shaped cross-section where said small-diametered cylindrical portion 14a is connected to said large-diametered cylindrical portion 14b at the side thereof.

Said atomizing means 10 is incorporated in the large-diametered cylindrical portion 14b side of the casing 10 and has a piezoelectric vibrator 10a and vibration liquid 10b. Said piezoelectric vibrator 10a is fixed at the lower end of a hollow cylindrical body 18 supported on a cover member 16 which closes the open end of the casing 10, so that the same is able to close the lower end of said hollow cylindrical body 18 via a protection sheet 19 and an attaching plate 20. Said vibration liquid 10b is, for example, distilled water, which is brought into contact with said protection sheet 19 secured on the upper surface of said piezoelectric vibrator 10a and is sealed in said cylindrical body 18 by adhering a film-shaped sheet 22 at the intermediate position of said hollow cylindrical body 18.

Said hollow cylindrical member 18 is fixed at one end side (the large-diametered cylindrical side 145b side of the casing 10) of said cover member 16 formed to be roughly gourd-shaped, so that the upper end thereof protrudes upward, and a through-hole 24 is formed at the other end side (the small-diametered cylindrical portion 14a side of the casing 10) of the cover member 16. A rotating axis of a motor 24 is inserted from below into said through-hole 24, and an impeller 28 is fitted from above to the inserted rotating axis.

Said motor 26 and impeller 28 have a smaller diameter than the inner diameter of the small-diametered cylindrical portion 14a of the casing 14, which constitute a feeding means for creating an air flow for sending atomized medicine toward to the nozzle 12 side. Power is supplied to the motor 24 through a control circuit mounted on a substrate 31.

A medicine disk 32 which accommodates liquefied medicine is fitted to the inner side of the portion where the hollow cylindrical body 18 protrudes above of the cover member 16. The medicine disk 32 of this preferred embodiment has a bottom face inclined downward as the detail thereof is shown in FIG. 3, and a gelled substrate 34 intervenes between the bottom and the film-like sheet 22. This gelled substance 34 is for increasing the atomization efficiency of liquefied medicine by improving the transmission state of vibrations and is composed of a polymer, a dampening agent, water, a preserving agent, a surface-active agent, etc.

On the other hand, one large-diametered through-hole 14*d* is formed at the front side of the gripping casing 14 and two small-diametered through-holes 14*e* are formed at the upper part thereof. Furthermore, a circular through-hole 14*f* is formed at the lower end of the side of the small-diametered cylindrical portion 14*a* of the casing 14. An operation switch 38 supported at a substrate 36 which is inserted into the rear side of the large-diametered through-hole 14*d* is inserted into the large-diametered through-hole 14*d*, and a switch cover 40 is attached to the inserted operation switch.

An indication lamp 41 supported at the substrate 36 is disposed at the rear side of the small-diametered through hole 14*e*, and said indication lamp 40 is concretely composed of two light emitting diodes, wherein the two light emitting diodes are provided so that they face the small-diametered through-hole 14*e* via a cover 42. Furthermore, one of the two light emitting diodes blinks corresponding to turning on and off of the operation switch 38 and the other of them is lit when it becomes necessary for a secondary battery to be charged.

A connector 44 is attached to the rear side of the circular through-hole 14*f*, and an adapter 88 connected to a commercial power source is inserted into this connector 44. With the above construction, the operation switch 38 is disposed at the portion where the small-diametered cylindrical portion 14*a* of the casing 14 is connected to the large-diametered cylindrical portion 14*b* thereof, and the indication lamp 41 is provided in the vicinity of this operation switch 38.

The cover member 16 is fitted to and fixed at the upper opening end of the casing 14 so that a part of the upper side thereof protrudes therefrom, and a transparent cover 46 is detachably attached from above to the protruded portion. The cover 46 is composed of a transparent body of which the lower end is open, and the cross-section of the cover 46 is formed to be gourd-shaped equivalently to the shape of the casing 14. Furthermore, the cover 46 has a small-diametered circumferential wall 46a and a large-diametered circumferential wall 46*b* respectively having diameters corresponding to that of the small- and large-diametered cylindrical portions 14*a* and 14*b*, and a ceiling part 46*c*.

A circular through-hole 46*d* which passes through the ceiling part 46*c* is provided at the ceiling part 46 on the center of the large-diametered circumferential wall 46*b*, and at the same time, a nozzle attaching port 46*e* protruding upward is provided at the surrounding of the circular through-hole 46*d*. Furthermore, an annular protrusion 46*f* protruding downward is provided outside the nozzle attaching portion 46*e*.

Furthermore, a roughly semi-circular opening part 46*g* is formed to be open at the upper side of the small-diametered circumferential wall 46*a*, a circular ledge 46*h* linked to the inner face of the small-diametered circumferential wall 46*a* is formed at the lower end inner circumferential side of said opening part 46*g*. And a circular through-hole 46*i* is formed and is caused to pass through the center of said ledge 46*h*, and a plurality of slits 46*j* are provided at the outer circumference of said circular through-hole 46*i*. At the deep side of the ledge 46*h*, an arcuate wall 46*k* of which the upper end is linked to the ceiling part 46*c* is formed. Furthermore, a small-diametered through-hole 46*l* is formed at the ceiling part 46*c* corresponding to the center of the circular through-hole 46*i*. On the other hand, a rectifying member 48 of atomized medicine is attached from above to the hollow cylindrical member 18. Said rectifying member 48 is composed of a flange part 48*a* attached to the upper end side of the hollow cylindrical member 18, a guide cylindrical part 48b integrally formed at the inner circumference of this flange part 48a with both the ends, the upper end side of which is fitted to and fixed at the annular protrusion 46f, a dome portion 48c supported at the inner circumferential side of said guide cylindrical part 48b, and a pair of slits secured at the position opposite said guide cylindrical part 48c.

In this preferred embodiment, said dome portion 48c is constructed of a semi-spherically formed large spherical portion 481c and a small spherical portion 482c formed at the upper end of said large spherical portion 481c. The large spherical portion 481c is disposed on the center axis of said guide cylindrical part 48b and is formed with the diameter by which the outer circumference thereof is spaced from the inner circumferential face of the guide cylindrical part 48b. Two points of the large spherical portion 481c opposite each other are supported by a pair of stays 48e extending in the tangential direction, whereat a slit hole 48d is provided.

Furthermore, a pair of wall parts 48f located forward of the slits 48d are oriented in the diametrical direction of the large-spherical portion 481c and are provided between the large-spherical portion 481c and the guide cylindrical portion 48b. With the rectifying member 48 constructed as shown above, the medicine atomized from the medicine disk 32 is caused to move upward and is brought into collision with the dome portion 48c, and the liquefied medicine brought into collision with the spherical inner surface of the dome portion 48c is thereafter reflected toward the center of the dome portion 48c and is mixed with the atomized medicine which is gradually caused to go up, in the dome portion 48c. Thereafter, the mixed medicine is sent out to the nozzle 12 side together with an air flow introduced via the slits 48d and created by the impeller 28 between the inner circumferential face of the guide cylindrical portion 48b and the outer circumferential portion of the dome 48c so as to bypass at the lower end of the dome portion 48c.

On the other hand, an air flow regulating member 50 is attached in the opening portion 46g. Said air flow regulating member 50 is formed to be cap-like. A filter 52 is disposed on the inner circumferential face of the circumferential wall 50a thereof, and at the same time, a hole 50b extending in the circumferential direction and a slide grip 50c are provided at the circumferential wall 50a, and at the same time, a small-diametered protrusion 50d protruding upward is provided at the center of the ceiling part. This air flow regulating member 50 is positioned and mounted by the small-diametered protrusion 50d into the small-diametered through-hole 461 of the cover 46, and by causing the air flow regulating member 50c to move in the circumferential direction with said slide grip 50c, the hole 50b changes the length of a portion which is exposed to the opening portion 46g, whereby the air flow created by the impeller 28 is regulated.

The nozzle 12 is constructed of a transparent rubber-based member in this preferred embodiment, and is mounted by placing the base part thereof at the nozzle attaching port 46e of the cover 46. At this time, it is possible to optionally change the discharging direction of the atomized medicine by changing the fitting state of the base part. Furthermore, in the case of this preferred embodiment, since the nozzle 12 is made of a soft rubber based member, it is possible to change the discharging direction by turning the nozzle 12 in a state where the same is fitted to the nozzle attaching port 46e.

A notched section 46m which is able to be fitted to the cap 54 attached from above the the cover 46 is formed at the outer circumferential edge of the ceiling part 46c of the cover 46. The cap 54 has a circumferential wall part 54a having the same cross-section as that of the casing 14 and a ceiling part 54b. A concave portion 54c which is able to be fitted with the gourd-shaped convex part 14g secured at the lower end side of the casing 14 is formed at the outer circumferential edge of the ceiling part 54b.

A switch 70 is provided between the grip casing 14 and the cover 46. Said switch 70 is composed of a switch accommodating section 72 secured at the box member 16 which closes the upper end opening of the grip casing 14, a switch operating section 74 provided to protrude at the inner circumferential face of the cover 46, and a switch body 76 accommodated in the switch accommodating section 72.

Said switch accommodating section 72 is disposed in the vicinity of the connection part at which the small-diametered cylindrical portion 14a of the grip casing 14 is linked with the large-diametered cylindrical portion 14b thereof and is formed to be square-tubular with both the ends thereof open. Said switch operating section 74 is provided at the switch accommodating section 72 corresponding to the position thereof, wherein a waterproof cover 78 which covers the outer circumference of the switch accommodating section 72 is provided at the lower end of the switch operating section 74. Said switch body 76 consists of a switch mechanism 76a having a pair of always open contacts spaced from each other in a constant state, a rod 76b interlocked with said switch mechanism 76a, and a spring 76c which always presses the rod 76b upward.

Figure 1:
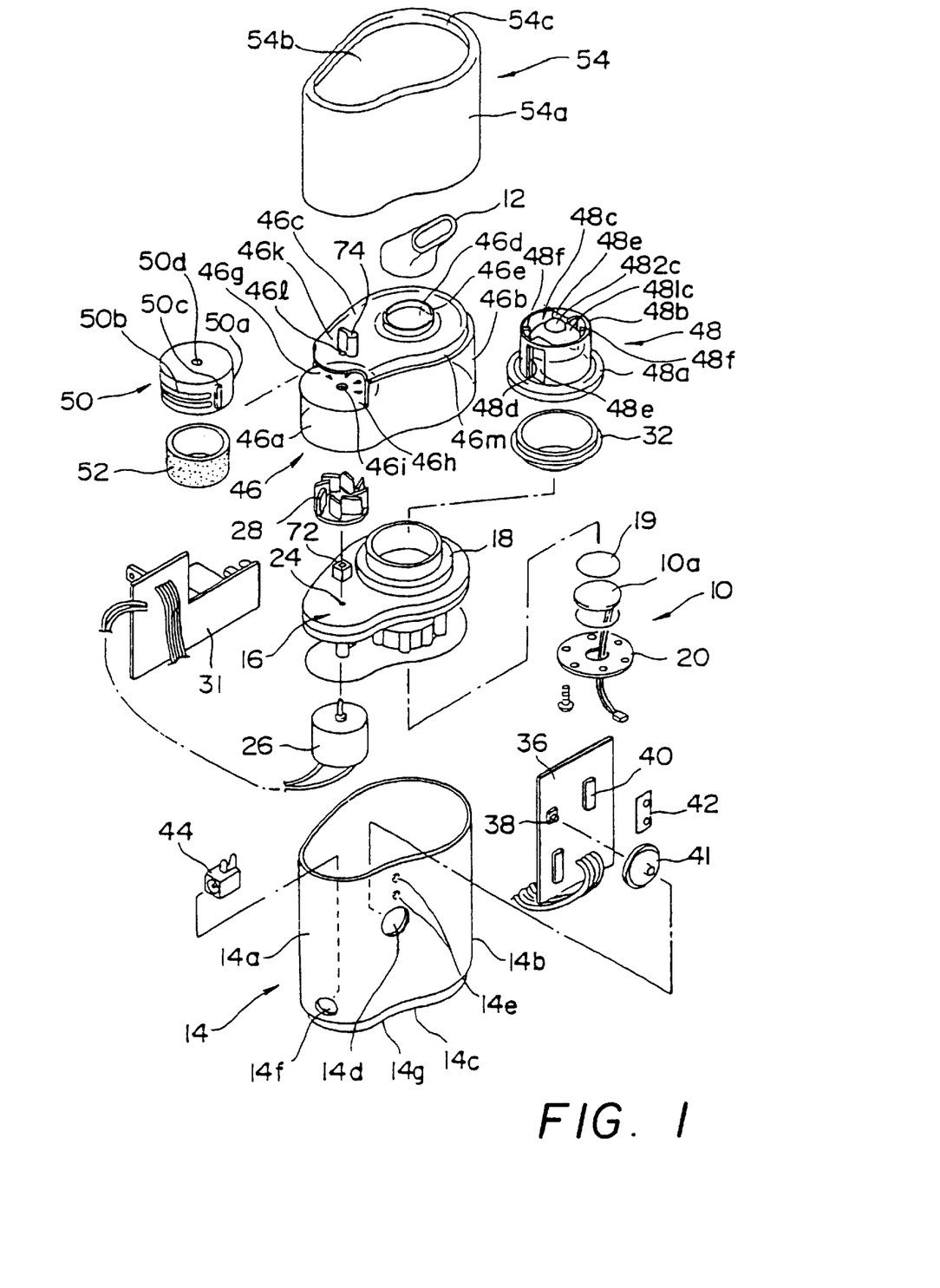
FIG. 1 is a disassembled perspective view showing a preferred embodiment of a handy type atomizer according to the invention.
Figure 2:
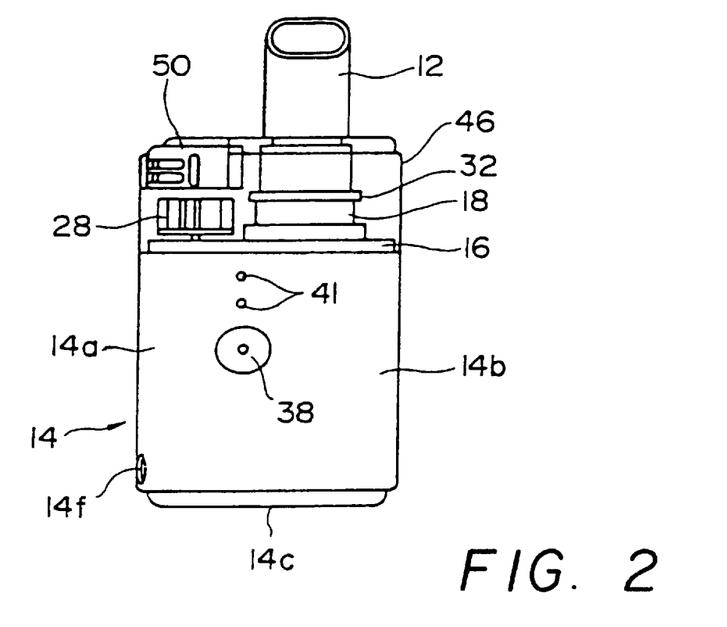
FIG. 2 is a front elevational view showing an atomizer of FIG. 1 assembled with its cap removed.
Figure 3:
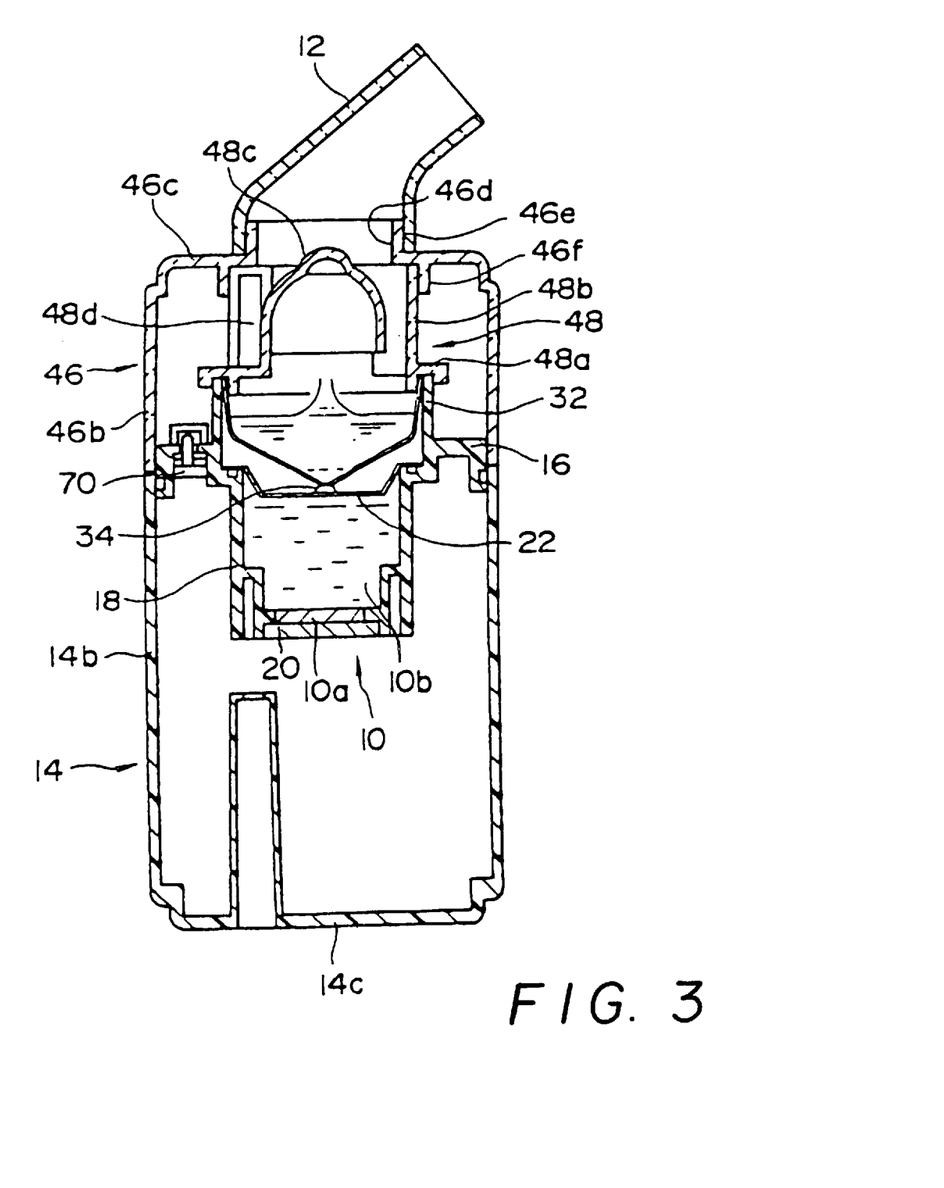
FIG. 3 is a longitudinally sectional view of FIG. 2.
Figure 4:
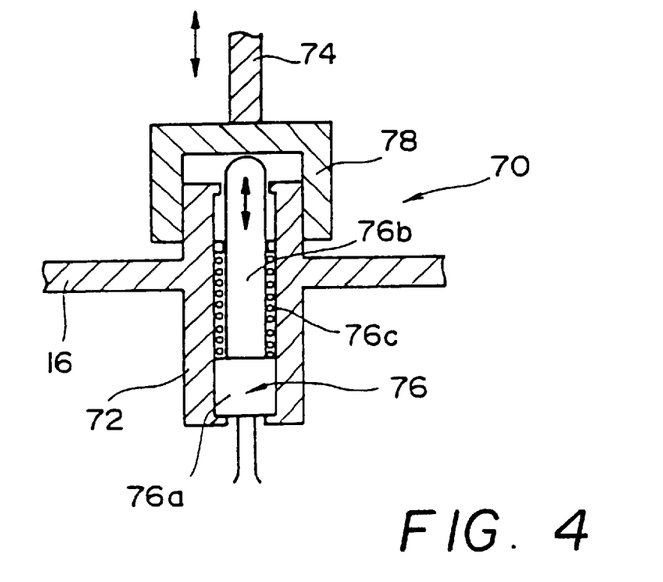
FIG. 4 is an enlarged view of major parts of FIG. 2.
Figure 5:
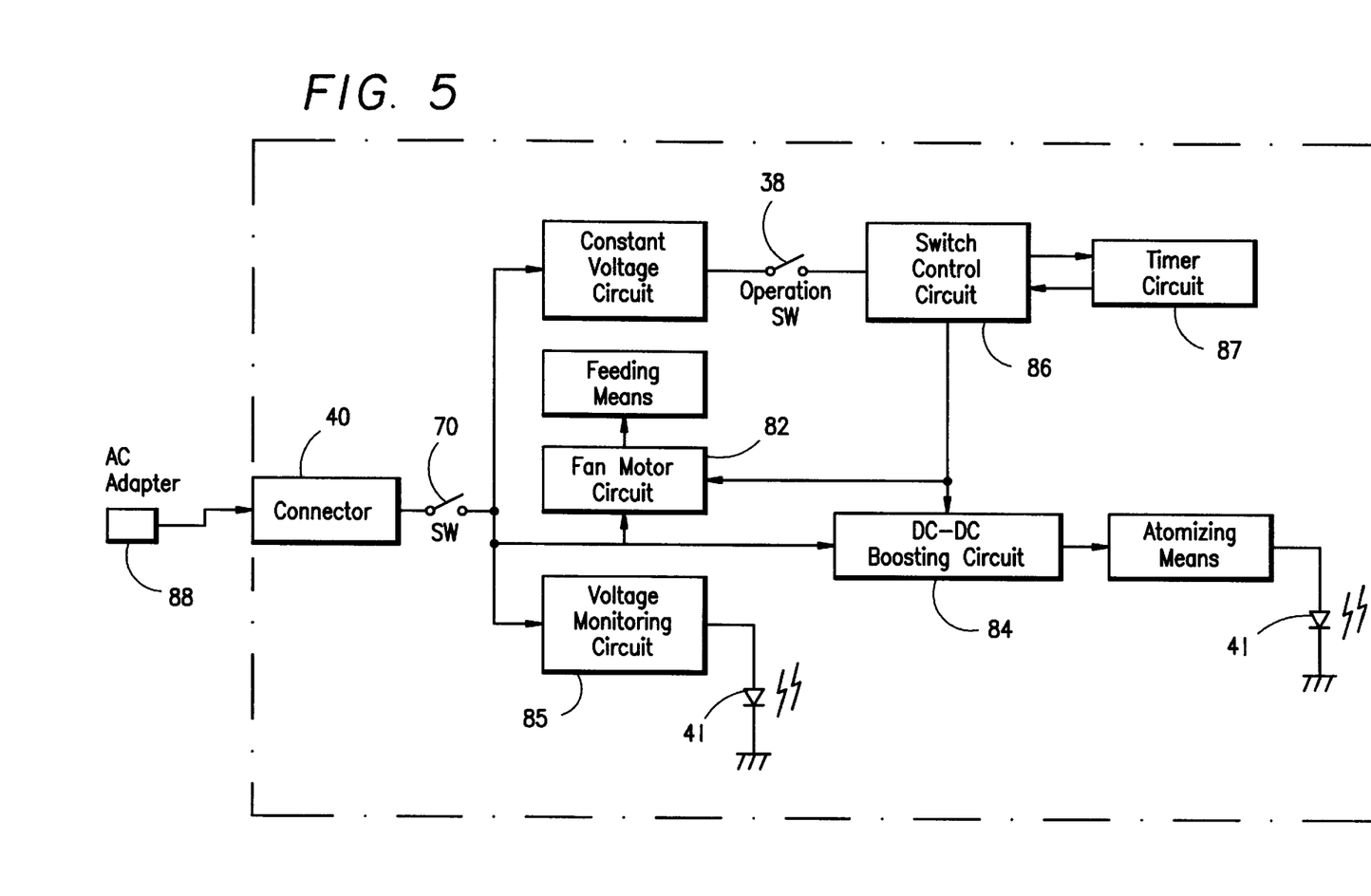
FIG. 5 is a block diagram of control circuits of an atomizer shown in FIG. 1.

With the switch 70 constructed as described above, if the rod 76b is pressed down against the pressing force of the spring 76c by using the switch operating section 74, the contact of the switch mechanism 76a is electrically connected. FIG. 5 is a block diagram of a control circuit incorporated in the substrate 31 of the abovementioned atomizer. The control circuit shown in the same drawing consists of a switch 70 connected in series to the connector 44, a constant voltage circuit 80, a fan motor drive circuit 82, a boosting circuit 84, and a voltage monitoring circuit 85 which are connected in parallel to the switch 70, and a switch control circuit connected to the output side of the constant voltage circuit 80 via the operating switch 38.

A motor 26 of the feeding means is connected to the output side of the fan motor circuit 82. The piezoelectric vibrator 10a of the atomizing means 10 and a display 41 are connected to the output side of the boosting circuit 84. The display 41 is connected to the output side of the voltage monitoring circuit. A monitoring circuit 87 by which the operation time of the atomizer is set is connected to the switch control circuit 86. An appointed direct current is supplied to the connector 44 via an AC adapter 88 incorporated in a secondary battery.

Hereupon, with a handy type atomizer constructed as described above, by placing liquefied medicine in a medicine disk 32 and turning on the operating switch 38, the vibrations of said piezoelectric vibrator 10b are transmitted to the liquefied medicine via a vibration liquid 10b, whereby the liquefied medicine is atomized, and the atomized medicine is discharged through the nozzle 12 along with an air flow created by the impeller 28.

At this time, an atomizer according to the preferred embodiment is able to operate only when a detachable cover 46 is attached to the gripping casing 14. Since a switch 70 which supplies power to the motor 26 of the atomizing means 10 and the feeding means is provided, the switch 70 enters a non-operating state in a case where the cover 46 is removed from the casing 14 or the same is incompletely attached thereto, no power is supplied to the motor 26 of the atomizing means 10 and the feeding means.

Figure 6:
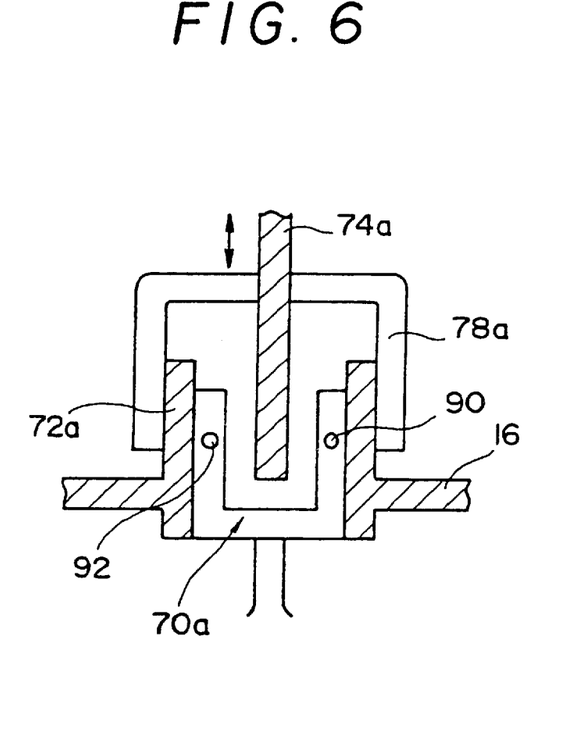
FIG. 6 is a cross-sectional view of major parts showing another preferred embodiment of an atomizer according to the invention.

Accordingly, the atomized medicine is prevented from being discharged outside other than through the nozzle 12, and the atomized medicine is prevented from being uselessly consumed, whereby the safety of an atomizer is much increased. FIG. 6 shows another preferred embodiment of an atomizer according to the invention. Only the features thereof are described below. The drawing shows a switch 70*a* to be provided between a cover 46 detachably attached to the casing 14 and the cover member 16. In this preferred embodiment, an optical type photocoupler in which a light emitting part 90 and a light receiving part 92 are disposed opposite each other is used.

The switch 70*a* is disposed in the switch accommodating section 72*a* secured at the cover member 16, and the switch operating section 74*a* secured at the cover 46 is constructed so that the switch 70*a* is able to be operated by interrupting light between the light emitting part 90 and the light receiving part 92. Furthermore, the switch operating section 74*a* is provided with a waterproof cover 78*a* which is able to cover the upper end side of the switch accommodating section 72*a*.

Even by using a switch 70*a* constructed as described above, the actions and effects which are identical to those of the preceding preferred embodiment can be obtained. Furthermore, in the above preferred embodiments, such a type which is composed of a piezoelectric vibrator 10 and a sealed vibration liquid 10*b* is illustrated and described as a medicine atomizing means. The invention is not limited to this type. For example, a heating means such as a heater may be employed instead. Industrial feasibility As described in detail with reference to the preferred embodiments, with a handy type atomizer according to the present invention, it is possible to prevent the atomized medicine from being uselessly discharged outside and to increase the safety thereof.

What is claimed is:

1. A handy atomizer having a liquefied medicine atomizing means, a nozzle for discharging the atomized medicine outside and a feeding means for sending out the medicine atomized by said atomizing means toward said nozzle side, comprising a gripping casing in which said atomizing means is incorporated, and a cover detachably attached to the upper end of said gripping casing and having an attaching part of said nozzle, a first switch for selectively supplying power to said atomizing means and said feeding means, and a second switch for enabling said first switch to operate only when said cover is attached to said gripping casing.

2. The handy atomizer of claim 1, wherein said second switch is disposed between said casing and said cover, and is electrically connected to said first switch.

3. The handy atomizer of claim 2, wherein said second switch includes a spring-biased member which is depressed to close said second switch when said casing and cover are attached.

4. The handy atomizer of claim 2, wherein said second switch includes a light source adjacent to a photosensitive element, and wherein a path between said source and element is broken when said casing and cover are attached to close said second switch.

* * * * *